United States Patent
Tomita et al.

(10) Patent No.: US 6,374,131 B1
(45) Date of Patent: *Apr. 16, 2002

(54) BIOMAGNETISM MEASURING METHOD AND APPARATUS

(75) Inventors: Sadamu Tomita; Keisuke Toyama, both of Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/362,570

(22) Filed: Jul. 28, 1999

(51) Int. Cl.$^7$ .............................................. A61B 5/05
(52) U.S. Cl. ..................... 600/409; 324/244; 324/248; 324/252; 324/260
(58) Field of Search ..................... 600/409; 324/244, 324/248, 252, 260

(56) References Cited

U.S. PATENT DOCUMENTS

| | | | | |
|---|---|---|---|---|
| 3,980,076 A | * | 9/1976 | Wikswo, Jr. et al. | 600/409 |
| 4,079,730 A | * | 3/1978 | Wikswo, Jr. et al. | 600/410 |
| 4,793,355 A | * | 12/1988 | Crum et al. | 600/409 |
| 5,269,325 A | * | 12/1993 | Robinson et al. | 600/409 |
| 5,285,385 A | * | 2/1994 | Igarashi et al. | 600/409 |
| 5,755,227 A | * | 5/1998 | Tomita et al. | 324/244 |
| 5,762,611 A | * | 6/1998 | Lewis et al. | 600/544 |

OTHER PUBLICATIONS

Robinson et al, "Current Source Image Estimation by Spatially Filtered MEG", Biomagnetism:Clinical Aspects, 1991, pp. 761–765.

* cited by examiner

Primary Examiner—Marvin M. Lateef
Assistant Examiner—Jeoyuh Lin
(74) Attorney, Agent, or Firm—Rader, Fishman & Grauer, PLLC (57) ABSTRACT

A technique for accurately determining states of bioelectric currents occurring in particular positions in a site of interest of a patient. Transfer functions between the particular positions and each magnetic sensor are derived from a positional relationship between the site of interest and each magnetic sensor. Weight coefficients are computed from an inverse matrix obtained by adding a predetermined value to a matrix of the transfer functions, and virtual biomagnetism information obtained virtually by bioelectric currents set to the particular positions. Enhanced biomagnetism information with only the biomagnetism from the particular positions enhanced is acquired by superposing the weight coefficients of measured biomagnetism information. Based on this enhanced biomagnetism information, states of bioelectric currents occurring in the particular positions are determined accurately.

18 Claims, 7 Drawing Sheets

BIOMAGNETISM MEASURING METHOD AND APPARATUS

BACKGROUND OF THE INVENTION (1) Field of the Invention

This invention relates to a biomagnetism measuring method and apparatus for determining bioelectric currents occurring in a site of interest in the body of an examinee or patient.

(2) Description of the Related Art

A living body produces minute biomagnetism as a result of bioelectric currents occurring in the living body. For example, the biomagnetism generated by bioelectric currents in the brain is called magnetoencephalo which includes induced magnetoencephalo formed by a stimulation applied to the living body, and spontaneous magnetoencephalo produced spontaneously by the brain such as alpha wave or spike wave associated with epilepsy.

In recent years, a multichannel SQUID sensor has been developed which uses SQUIDs (Superconducting Quantum Interface Devices) as magnetic sensors for measuring minute biomagnetism in the living body. The multichannel SQUID sensor has a multiplicity of magnetic sensors immersed in a coolant such as liquid nitrogen within a vessel called a Dewar. The magnetic sensors have coil portions for measuring magnetic fields, and SQUID sensor portions for converting the magnetic fields detected to voltages.

The multichannel SQUID sensor is placed outside a site of interest, e.g. the head, of a patient. The magnetic sensors in the multichannel SQUID sensor can carry out a noninvasive measurement of minute biomagnetism produced by bioelectric currents occurring in the brain. From biomagnetism information thus obtained, one can grasp locations, orientations and other states of the bioelectric currents occurring in the site of interest of the patient.

Conventionally, bioelectric currents formed in a patient's site of interest are derived as follows.

First, a positional relationship between the multichannel SQUID sensor and patient's site of interest is determined. There are various techniques for determining the positional relationship as disclosed in Japanese Patent Publication (Unexamined) H5-237065 and Japanese Patent Publication (Unexamined) H6-788925, for example.

Next, weight coefficients are computed which will enhance biomagnetism information based on a minute magnetic field formed by a bioelectric current flowing in each particular position in the patient's site of interest. These weight coefficients are computed for each magnetic sensor included in the multichannel SQUID sensor. A technique for computing the weight coefficients is described, for example, in S. E. Robinson and D. F. Rose, "Current Source Image Estimation by Spatially Filtered MGE", Biomagnetism: Clinical aspects (1992).

A computation of convolution is carried out of biomagnetism information acquired by measuring the biomagnetism from the patient's site of interest, and the weight coefficients for enhancing only the biomagnetism from each particular position. As a result, only the biomagnetism generated from the bioelectric currents in the particular position in the site of interest is enhanced. In this way, bioelectric currents in given positions in the patient's site of interest may be determined.

By determining the states of bioelectric currents for numerous positions in the patient's site of interest, the states of bioelectric currents occurring in the entire site of interest may be grasped. These bioelectric currents may be superposed on a tomographic image of the patient's site of interest acquired with an MRI apparatus or the like, to grasp the states of bioelectric currents on the tomographic image of the site of interest.

However, in order to enhance the biomagnetism from the bioelectric current occurring in each particular position in the patient's site of interest, according to the prior art, a weight coefficient must be computed for application to each transfer constant, which will equalize the bioelectric current expressed by delta function set to the particular position in the site of interest, to a sum total of transfer constants with which the magnetic field is transmitted from the particular position to the respective magnetic sensors. This weight coefficient is computed from an inverse of a matrix based on a transfer constant for each magnetic sensor, and virtual biomagnetism information measured virtually by each magnetic sensor when the bioelectric current expressed by delta function is set to the particular position. However, when the solution of the matrix based on the transfer constant is very close to zero, the solution of the inverse matrix becomes enormous. With the weight coefficients computed from this inverse matrix and applied to the measured biomagnetism information, even the noise included in the information is enhanced. It is therefore impossible to grasp accurately the bioelectric currents occurring in the particular positions.

SUMMARY OF THE INVENTION

This invention has been made having regard to the state of the art noted above, and its object is to provide a biomagnetism measuring method and apparatus for accurately determining bioelectric currents occurring in particular positions in a patient's site of interest, without being affected by noise included in measured biomagnetism information.

This above object is fulfilled, according to this invention, by a biomagnetism measuring method for measuring, with a plurality of magnetic sensors arranged adjacent a site of interest of a patient, biomagnetism generated from bioelectric currents flowing in the site of interest, and determining the bioelectric currents based on measured biomagnetism information acquired through the measurement, the method comprising the steps of:

computing transfer constants indicating degrees by which the biomagnetism is transferred from each particular position in the site of interest to each of the magnetic sensors;

regulating a matrix of the transfer constants;

computing a weight coefficient for each of the magnetic sensors to enhance biomagnetism generated from the particular position, based on virtual biomagnetism information virtually measured by the magnetic sensors and an inverse matrix of the regulated matrix, when a known bioelectric current is set to the particular position;

collecting measured biomagnetism information acquired by measuring the biomagnetism generated from the site of interest with the magnetic sensors;

computing enhanced biomagnetism information having the biomagnetism generated from the particular position enhanced by applying the weight coefficient to the measured biomagnetism information measured by each of the magnetic sensors; and determining a bioelectric current in the particular position based on the enhanced biomagnetism information.

According to this invention set out above, a transfer function indicating a degree of transfer of biomagnetism in space is determined based on Biot-Savart's law, for example. Transfer constants are obtained by substituting, for the transfer function, particular positions in the site of interest of the patient and positional relationships thereof with the respective magnetic sensors. A matrix formed of the transfer constants is regulated, whereby a solution of the matrix has a value remote from zero. This lessens the unstable condition of the matrix occurring when the solution of the matrix is very close to zero. Further, a weight coefficient is computed for each of the magnetic sensors to enhance biomagnetism generated from each particular position, based on virtual biomagnetism information virtually measured by the magnetic sensors and an inverse matrix of the regulated matrix, when a known bioelectric current is set to the particular position. These weight coefficients, which are based on an inverse matrix in a stabilized condition, enhance only the biomagnetism from the particular positions. Then, enhanced biomagnetism information is computed by applying the weight coefficients to the measured biomagnetism information obtained by measuring, with the magnetic sensors, the biomagnetism generated from the site of interest of the patient. The bioelectric currents in the particular positions are determined based on the enhanced biomagnetism information. Thus, this invention can avoid the inconvenience encountered in the prior art in which weight coefficients based on the inverse of a matrix whose solution is close to zero are applied to the measured biomagnetism information, thereby enhancing even noise included in the measured biomagnetism information. As a result, the invention enables a correct determination of the states of bioelectric currents, e.g. current sizes, directions and locations, in particular positions in a patient's site of interest.

Preferably, the method according to this invention further comprises the step of outputting an arrow map showing the bioelectric current in each particular position in form of an arrow, the step of outputting an arrow map showing the bioelectric current in each particular position in form of an arrow, as superposed on a tomographic image including the particular position, the step of outputting an intensity distribution chart of the bioelectric currents generated in the site of interest, or the step of outputting a waveform chart of biomagnetism measured by each of the magnetic sensors. This method will then facilitate a visual recognition of the states of bioelectric currents in the particular positions in the patient's site of interest or the states of biomagnetism measured. This feature is of advantage to diagnostic situations and the like.

It is preferred that the matrix regulating step is executed to add a predetermined value for a solution of the matrix of the transfer constants to be remote from zero. The predetermined value, preferably, is at least one of a unit matrix or a penalty matrix having a predetermined size. It is also preferred that the predetermined value is at least one of a unit matrix or a penalty matrix having a size corresponding to noise included in the measured biomagnetism information.

In another aspect of this invention, a biomagnetism measuring apparatus is provided for measuring, with a plurality of magnetic sensors arranged adjacent a site of interest of a patient, biomagnetism generated from bioelectric currents flowing in the site of interest, and determining the bioelectric currents based on measured biomagnetism information acquired through the measurement, the apparatus comprising:

a plurality of magnetic sensors arranged adjacent the site of interest;

a transfer constant computing device for computing transfer constants indicating degrees by which the biomagnetism is transferred from each particular position in the site of interest to each of the magnetic sensors;

a regulating device for regulating a matrix of the transfer constants;

a weight coefficient computing device for computing a weight coefficient for each of the magnetic sensors to enhance biomagnetism generated from the particular position, based on virtual biomagnetism information virtually measured by the magnetic sensors and an inverse matrix of the regulated matrix, when a known bioelectric current is set to the particular position;

a measured information collecting device for collecting measured biomagnetism information acquired by measuring the biomagnetism generated from the site of interest with the magnetic sensors;

an enhanced biomagnetism information computing device for computing enhanced biomagnetism information having the biomagnetism generated from the particular position enhanced by applying the weight coefficient to the measured biomagnetism information measured by each of the magnetic sensors; and a bioelectric current computing device for determining a bioelectric current in the particular position based on the enhanced biomagnetism information.

With this apparatus, the weight coefficient computing device computes a weight coefficient for each of the magnetic sensors to enhance biomagnetism generated from the particular positions in the site of interest, based on an inverse matrix of the matrix regulated by the regulating device, and on virtual biomagnetism information. The bioelectric current computing device determines bioelectric currents in the particular positions based on the enhanced biomagnetism information obtained by applying the weight coefficients to the measured biomagnetism information.

Preferably, the apparatus according to this invention further comprises an output device for outputting an arrow map showing the bioelectric current in each particular position in form of an arrow, an arrow map showing the bioelectric current in each particular position in form of an arrow, as superposed on a tomographic image including the particular position, an intensity distribution chart of the bioelectric currents generated in the site of interest, or a waveform chart of biomagnetism measured by each of the magnetic sensors.

Preferably, each of the magnetic sensors employed in the apparatus according to this invention is a high-sensitivity magnetic sensor including, for example, a coil, and a superconducting quantum interference device connected to the coil.

The regulating device of the above apparatus may, for example, add a predetermined value for a solution of the matrix of the transfer constants to be remote from zero. Preferably, the predetermined value is at least one of a unit matrix or a penalty matrix having a predetermined size. It is also preferred that the predetermined value is at least one of a unit matrix or a penalty matrix having a size corresponding to noise included in the measured biomagnetism information.

The apparatus according to this invention may further comprise a stimulating device for applying at least one of an electric stimulation, an acoustic stimulation and an optical stimulation.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENT

A preferred embodiment of this invention will be described hereinafter with reference to FIGS. 1 through 6.

Figure 1:
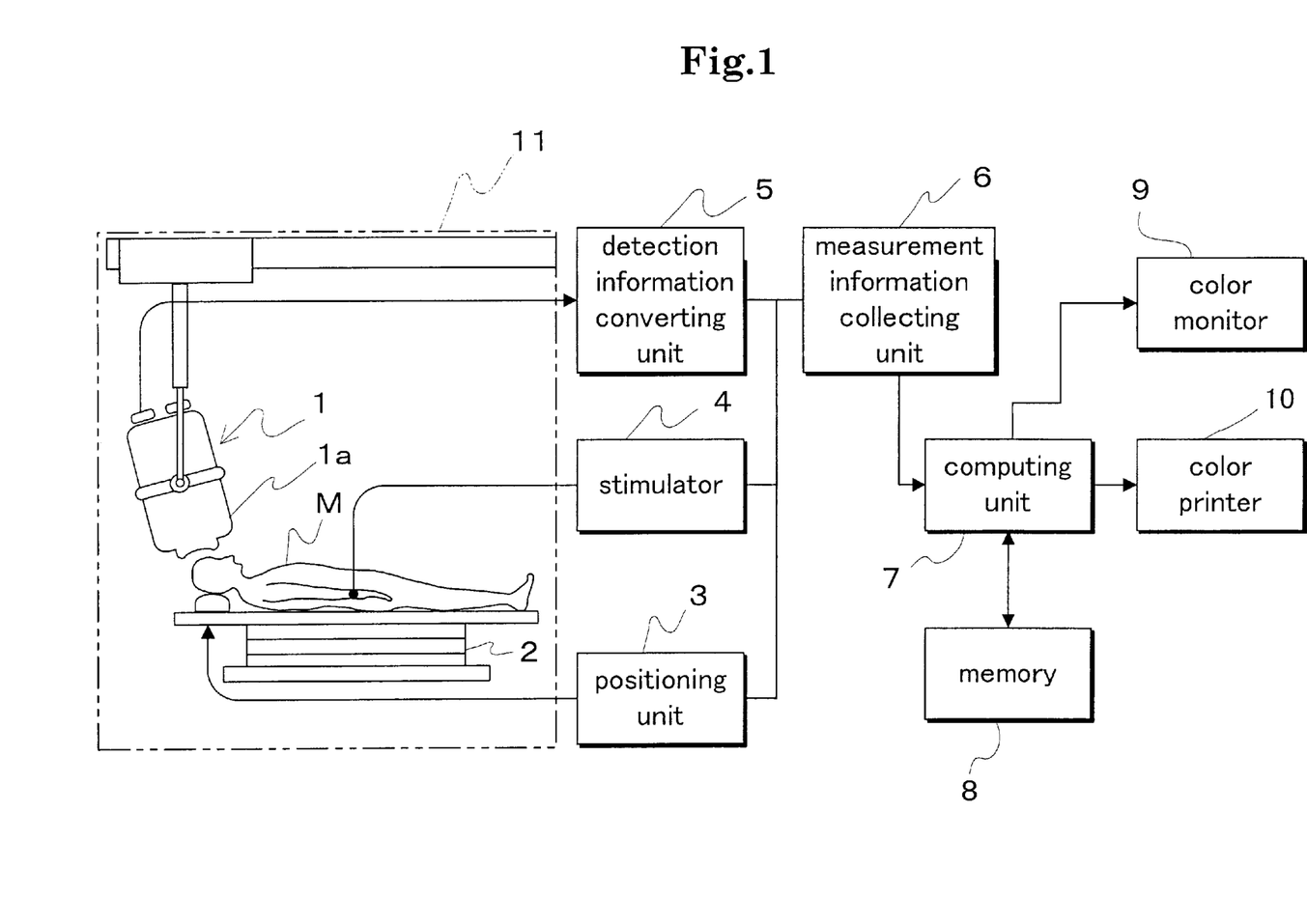
FIG. 1 is a block diagram showing an outline of a biomagnetism measuring apparatus according to this invention.

FIG. 1 is a block diagram showing an outline of a biomagnetism measuring apparatus embodying this invention. Numeral 11 in FIG. 1 denotes a magnetic shielded room. The magnetic shielded room 11 encloses a bed 2 for supporting a patient M lying thereon, and a multichannel SQUID sensor 1 (hereinafter called "fluxmeter 1") disposed adjacent a site of interest, e.g. the head, of the patient M. The fluxmeter 1 has a plurality (m) of magnetic sensors S1–Sm mounted in a Dewar 1a for performing a noninvasive measurement of minute biomagnetism formed by bioelectric currents occurring in the head.

Figure 3:
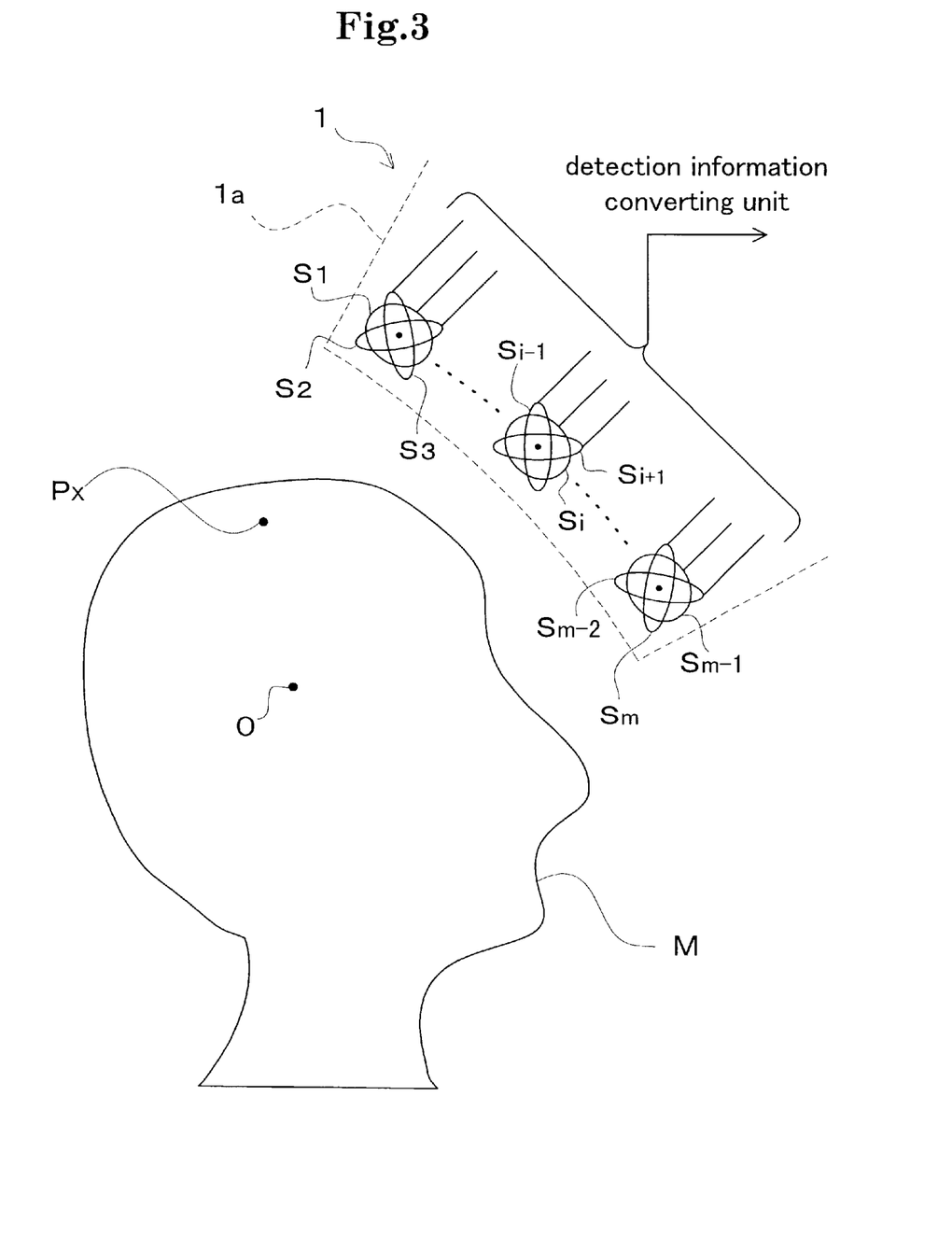
FIG. 3 is an enlarged view showing a fluxmeter and a patient's site of interest.

As shown in FIG. 3, the fluxmeter 1 has the m magnetic sensors S1–Sm immersed in a coolant such as liquid nitrogen stored in the Dewar 1a. The magnetic sensors S1–Sm have coil portions for detecting magnetic fields, and SQUID sensor portions, not shown, for converting the magnetic fields detected to voltages or currents. The magnetic sensors S1–Sm are what is known as vector type magnetic sensors, which are, for example, arranged in units of three having coil planes crossing one another at a predetermined angle in order to detect 3-D magnetic fields accurately.

Figure 4A:
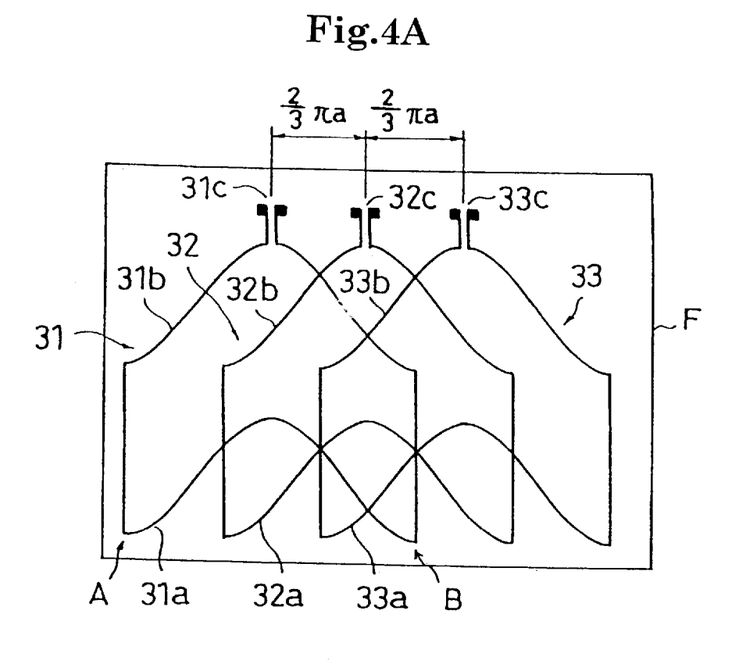
FIGS. 4A and 4B are views showing coils of magnetic sensors.
Figure 4B:
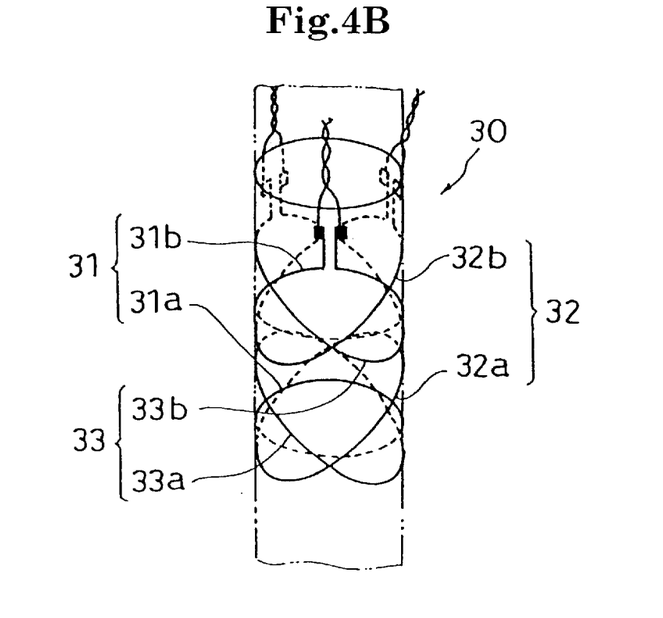

The magnetic sensors S1–S3, for example, have a construction shown in FIGS. 4A and 4B. FIG. 4A shows three coil pairs 31, 32 and 33 formed as electrically separated from one another on a film F. The coil pair 31, for example, includes two conductive patterns 31a and 31b expressed by a trigonometric function and having opposite ends connected through linear conductive patterns A and B. A joining terminal 31c is formed on the conductive pattern 31b. Other coil pairs 32 and 33 likewise include conductive patterns 32a, 32b, 33a, and 33b. The conductive patterns of the respective coil pairs 31, 32 and 33 are shifted sideways by $(2/3)\pi a$. Here, sign "a" is a radius of a coil bobbin described hereinafter.

The film F having the three coil pairs 31, 32 and 33 formed thereon are fixedly wrapped around the coil bobbin, such that the linear conductive patterns A and B lie close to each other. This state is shown in FIG. 4B. Thus, the conductive pattern 31a of the coil pair 31 forms a detecting coil, while the conductive pattern 31b forms a compensating coil, the coils being in a differential connection. The terminals 31c and 32c and 33c of the respective coil pairs 31, 32 and 33 are connected to the SQUID sensor portion. This invention is not limited to these coil pairs, but may employ a construction having coil planes crossing at right angles, for example.

A stimulator 4 applies an electric (acoustic, optical or other) stimulation to the patient M to generate bioelectric currents in the site of interest of the patient M. The magnetic sensors S1–Sm individually detect, as measured biomagnetism information, minute magnetic fields generated by the bioelectric currents. This measured biomagnetism information is converted into digital data by a detection information converting unit 5, which is then collected in a measurement information collecting unit 6. The measurement information collecting unit 6 corresponds to the measurement information collecting device of this invention.

A positioning unit 3 determines a positional relationship between the magnetic sensors S1–Sm and the site of interest of the patient M. For example, small coils are attached to a plurality of positions on the site of interest of the patient M, and the positioning unit 3 supplies power to these small coils. Then, the coils generate magnetic fields to be detected by the magnetic sensors S1–Sm, thereby to acquire coil position information. The positional relationship between the magnetic sensors S1–Sm and the site of interest of the patient M is grasped by analyzing the coil position information, Other techniques may be used to determine the positional relationship between the magnetic sensors S1–Sm and the site of interest of the patient M. For example, the patient M may be irradiated with light beams to determine the positional relationship. Various other methods are available as disclosed in Japanese Patent Publications (Unexamined) No. 5-237065 and No. 6-788925.

A computing unit 7 computes weight coefficients based on the positional relationship between the site of interest of the patient M and the magnetic sensors S1–Sm, and stores these weight coefficients in a memory 8. The weight coefficients are applied to the measured biomagnetism information detected by the magnetic sensors S1–Sm to acquire information on the direction, size and the like of a bioelectric current occurring in each particular position in the site of interest of the patient M. An image including this information and superposed on a tomographic image of the site of interest of the patient M and/or a picture showing the directions and sizes of bioelectric currents may be displayed on a color monitor 9 or outputted from a color printer 10. As will be apparent from the following description of operation, the computing unit 7 has functions corresponding to the transfer constant computing device, regulating device, weight coefficient computing device, enhanced biomagnetism information computing device, and bioelectric current computing device of this invention.

Figure 2:
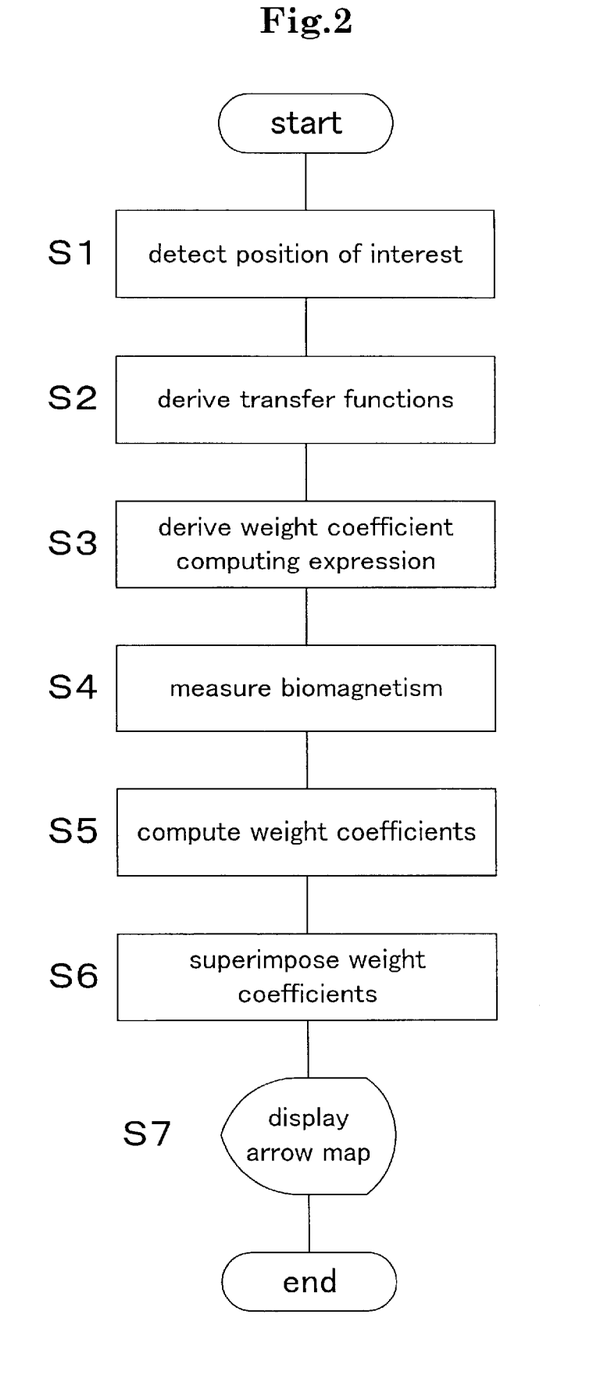
FIG. 2 is a flow chart of a processing sequence performed by the biomagnetism measuring apparatus.

Processes carried out by the respective components of the biomagnetism measuring apparatus will be described hereinafter with reference to the flow chart shown in FIG. 2.

Step S1 (Detect Position of Site of Interest)

First, the positioning unit 3 supplies an electric current to the plurality of small coils, not shown, attached to the head. The magnetic sensors S1–Sm detect magnetic fields formed by the respective small coils. The detection information converting unit 5 digitizes the magnetic fields detected, and transmits the information to the measurement information collecting unit 6 as coil position information.

Step S2 (Derive Transfer Functions)

Figure 5:
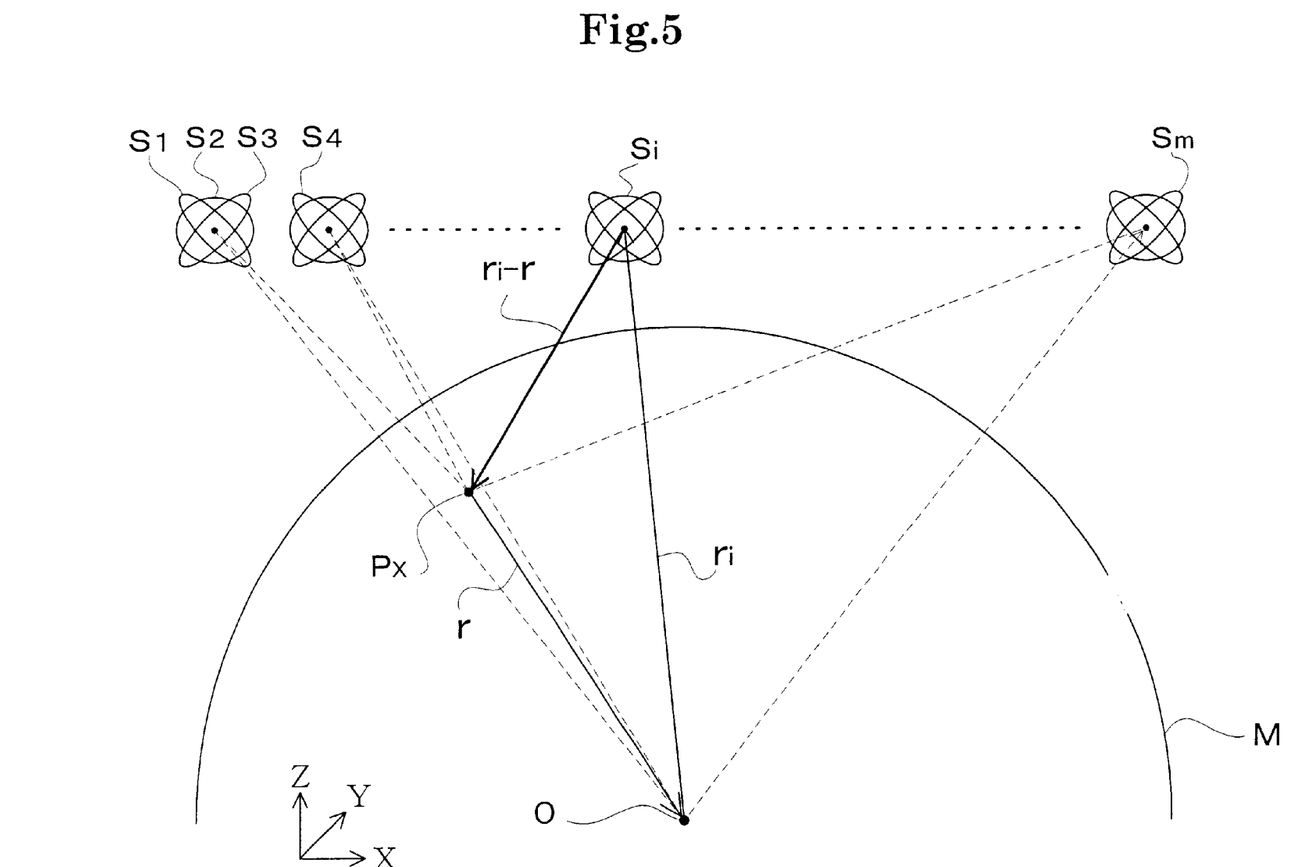
FIG. 5 is a view showing a relationship between each magnetic sensor and a particular position.

The computing unit 7 derives a positional relationship between the patient M and magnetic sensors S1–Sm from the coil position information transmitted to the measurement, information collecting unit 6. The positional relationship may be computed by using the least square method as in the prior art. When the positional relationship between the magnetic sensors S1–Sm and patient M has been derived, the computing unit 7 sets a 3-D coordinate system with a given position in the site of interest of the patient M regarded as origin O as shown in FIG. 5, for example. With this coordinate system, the computing unit 7 determines transfer functions indicating degrees by which the biomagnetism occurring, for example, from a particular position Px in the site of interest of the patient M reaches the magnetic sensors S1–Sm.

Where a bioelectric current exists in the particular position Px which is at a distance r from origin O as shown in FIG. 5, the computing unit 7 derives a transfer function Gi(r) indicating a degree of transfer of biomagnetism from the particular position Px to magnetic sensor Si, as follows. Where, for example, a bioelectric current J(r) (J(r) being a current density) exists in the particular position Px, the biomagnetism detected by the magnetic sensor Si may be expressed by the following equation (1) based on Biot-Savart's law:

$$Bi = \int_\Omega \frac{\mu_0}{4\pi} \frac{J(r) \times (r_i - r)}{|r_i - r|^3} e_i \, dr^3 \tag{1}$$

In equation (1), $\mu_0$ is magnetic permeability in a vacuum, ri is a distance from origin O to magnetic sensor Si, and ei is a unit normal vector passing through a coil plane of magnetic sensor Si. Therefore, Bi shows a flux density detected by the ith magnetic sensor. The above equation (1) is transformed into the following equations (2) and (3):

$$Bi = \int_\Omega J(r) \cdot G_i(r) dr^3 \tag{2}$$

$$Gi(r) = \frac{\mu_0}{4\pi} \frac{(r_i - r) \times e_i}{|r_i - r|^3} \tag{3}$$

As shown in equation (2), the flux density Bi may be expressed by an equation which integrates a scalar product of bioelectric current J(r) and Gi(r). Gi(r) in the above equation (3) is the transfer function from the particular position Px to the magnetic sensor Si. Step S2 corresponds to the function of the transfer constant computing device in this invention. Numerical values of the distance r of the particular position Px in the site of interest of the patient M from origin O and distances thereof to the magnetic sensors S1–Sm are substituted for the transfer function Gi(r) in equation (3) to obtain the transfer constants from the particular position in the site of interest to the respective magnetic sensors in this invention. The particular position Px in the site of interest of the patient M will be described hereinafter by using the transfer function Gi(r).

Step S3 (Derive Weight Coefficient Computing Expression)

The states of bioelectric currents existing in all positions in the site of interest of the patient M may be grasped accurately by enhancing only the biomagnetism occurring from the particular position Px and included in the measured biomagnetism information acquired by measuring biomagnetism from the entire site of interest. That is, by weighting the transfer function Gi(r) from the particular position Px to the magnetic sensors S1–Sm, the biomagnetism transferred based on the transfer function Gi(r) is enhanced. The computing unit 7 vitally sets an electric current δ(r) expressed by delta function (also called a unit size current or unit impulse) to the particular position Px. Further, the computing unit 7 sets an evaluation function f expressed by equation (4) set out below and including a weight coefficient Wi which equalizes the current δ(r) and a sum total of transfer functions G1(r)–Gm(r) from the particular position Px to the magnetic sensors S1–Sm. By setting this current δ(r) in a given one of the three-dimensional directions, it is possible to enhance components in the given direction of the bioelectric currents occurring from the site of interest of the patient M.

$$f = \int_\Omega \left[ \sum_{i=1}^m Gi(r) \cdot Wi - \delta(r) \right]^2 dr^3 \tag{4}$$

Next, to compute the weight coefficient Wi which minimizes the evaluation function f, equation (4) is differentiated to derive the following linear equation (5):

$$W = \Gamma^{-1} B \tag{5}$$

In equation (5), W is a matrix with the weight coefficient Wi serving as an element, $\Gamma^{-1}$ is a matrix with $\Gamma ij = \int Gi(r) Gj(r) dr^3$ serving as an element, and B is a matrix with $B = \int Gi(r) \delta(r) dr^3$ serving as an element.

The computing unit 7 adds, to the $\Gamma$ in the above equation (4), a value inputted beforehand by an operator through an input device not shown, which is, for example, λI corresponding to noise to be superimposed when measuring biomagnetism. λ represents a size of noise inputted, and I represents a unit matrix. The linear equation after λI is added is shown as weight coefficient computing equation W in the following equation (6):

$$W = (\Gamma + \lambda I)^{-1} B \tag{6}$$

With the above value λI added to Γ, the solution of matrix (Γ+λI) has a value remote from zero even where the solution of matrix Γ has a value very close to zero. That is, the regulated matrix (Γ+λI) is in what is known as a stable condition. The computing unit 7 stores this weight coefficient computing equation W in the memory 8. Step S3 corresponds to the function of the regulating device in this invention.

Step S4 (Measure Biomagnetism)

When the weight coefficient computing equation W has been derived, the computing unit 7 instructs the stimulator 4 to start a stimulation. The stimulator 4 gives the stimulation to the patient M to generate bioelectric currents in the site of interest. With the bioelectric currents, minute magnetic fields are generated from the site of interest of the patient M. The detection information converting unit 5 digitizes the biomagnetism detected by the magnetic sensors S1–Sm, and transmits it as measured biomagnetism information M1–Mm to the measurement information collecting unit 6. Step S4 corresponds to the function of the measurement information collecting device.

Step S5 (Compute Weight Coefficients)

The computing unit 7 substitutes, into the weight coefficient computing equation W, positions on the 3-D coordinate system of particular positions P1–Pn in the patient M designated beforehand by the operator, and computes weight coefficients to enhance biomagnetism from the particular positions P1–Pn. For the particular position P1, for example, weight coefficients P1W1–P1Wm are obtained to weight the measured biomagnetism information from the magnetic sensors S1–Sm. Similarly, weight coefficients P2W1–P2Wm to PnW1–PnWm are obtained for the particular positions P2–Pn. These weight coefficients are stored in the memory 8. Step S5 corresponds to the function of the weight coefficient computing device in this invention.

Step S6 (Superimpose Weight Coefficients)

The computing unit 7 reads weight coefficients PkW1–PkWm for a particular position Pk (k=1 to n) from the memory 8, and superimposes these weight coefficients PkW1–PkWm, respectively, on measured biomagnetism information M1–Mm collected in the measurement information collecting unit 6. This results in enhanced biomagnetism information DPk1–DPkm in which only the biomagnetism from the particular position Pk is enhanced. Further, enhanced bioelectric current Dk for the particular position Pk may be obtained by computing a sum total of enhanced biomagnetism information DPk1–DPkm. The computations carried out at step S6 are expressed by the following equation (7):

$$Dk = \Sigma(PkWm \cdot Mm) \quad (7)$$

Bioelectric currents D1–Dn for the particular positions P1–Pn are obtained by computing enhanced biomagnetism information based on equation (7) for the particular positions P1–Pn. Step S6 corresponds to the functions of the enhanced biomagnetism information computing device and bioelectric current computing device in this invention.

Step S7 (Display Arrow Map)

Figure 6:
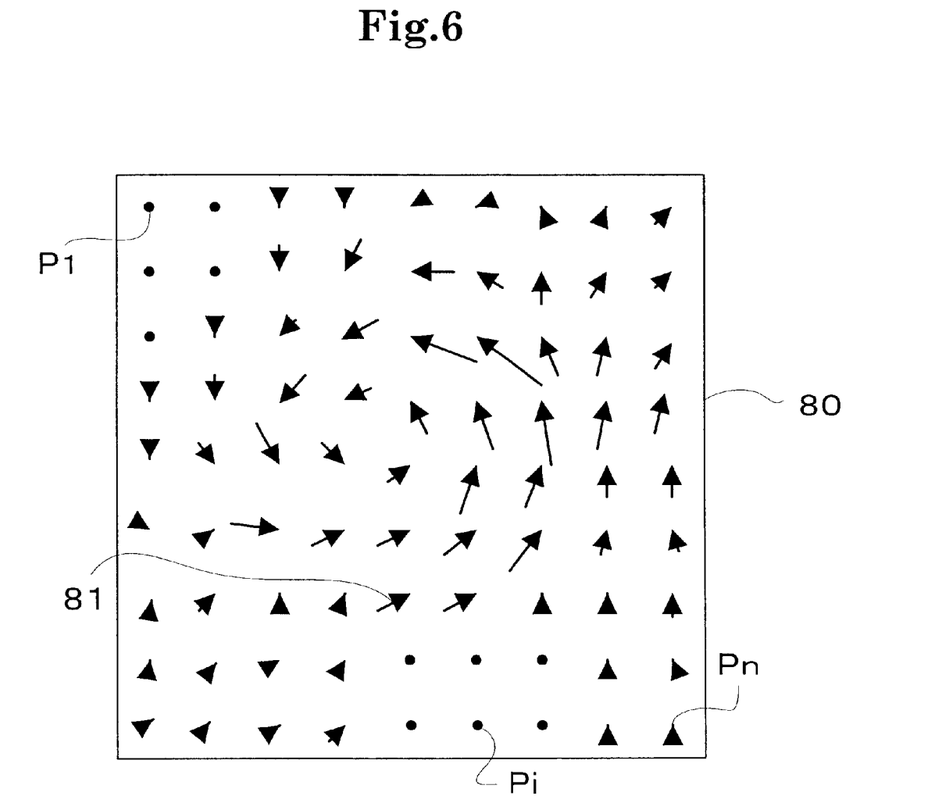
FIG. 6 is a view of an arrow map.

The bioelectric currents D1–Dn obtained at step S6 may be handled as vectors with current directions and sizes, and may therefore be displayed as bioelectric currents existing in the particular positions P1–Pn in the site of interest of the patient M. The computing unit 7 causes the color monitor 9 to display, or the color printer 10 to print out, what is known as an arrow map 80 as shown in FIG. 6, for example, which includes the particular positions P1–Pn arranged on a plane, along with vectors 81 for the respective particular positions P1–Pn. Step S7 corresponds to the function of the output device in this invention.

By observing the arrow map obtained as described above, the operator may accurately grasp the directions and sizes of bioelectric currents occurring in given positions in the site of interest of the patient M. By superposing the arrow map on a tomographic image of the site of interest of the patient M, the operator may grasp locations, directions and sizes of the bioelectric currents on the tomographic image.

Figure 7:
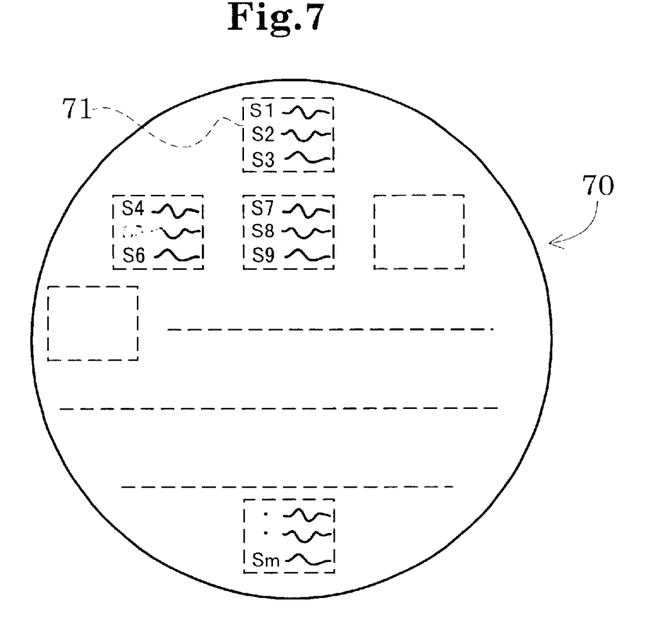
FIG. 7 is a view showing a waveform of biomagnetism measured by each magnetic sensor.

In this embodiment, the bioelectric currents are shown in the form of arrow map 80. As shown in FIG. 7, a waveform representation 70 may be employed to show the biomagnetism measured by each magnetic sensor in the form of a waveform. Reference numeral 71 in FIG. 7 denotes a single vector type magnetic sensor formed of magnetic sensors S1–S3. The waveforms included in the range corresponding to the vector type magnetic sensor 71 show time-dependent changes in the intensity of biomagnetism measured by the respective magnetic sensors S1–S3. While FIG. 7 shows three waveforms each, these waveforms may be superposed on one another or may be combined into a composite waveform.

Figure 8:
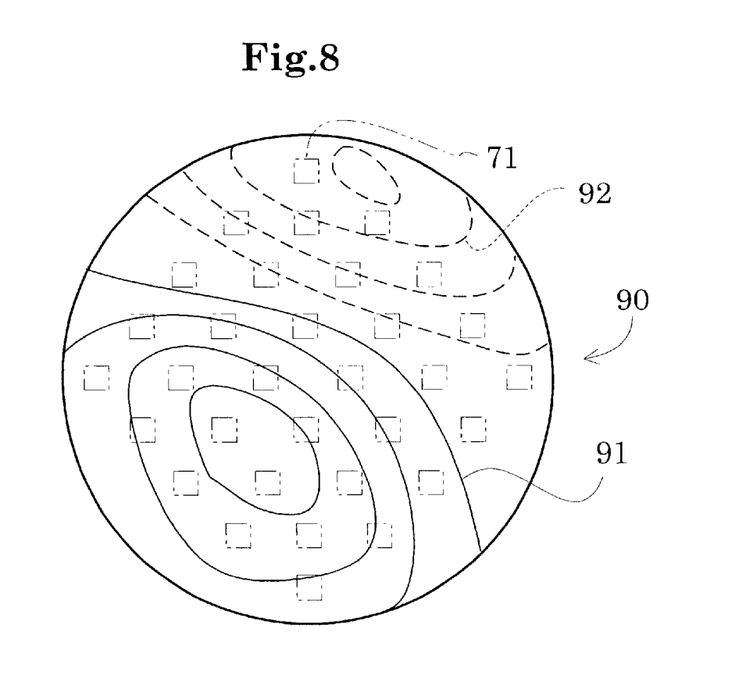
FIG. 8 is a view showing an intensity distribution of biomagnetic currents.

Further, in this embodiment, as shown in FIG. 8, an intensity distribution chart 90 may be displayed which, based on the biomagnetism measured by each magnetic sensor, shows an intensity distribution of bioelectric currents generated in the site of interest. In the intensity distribution chart 90, locations of high intensity are shown in red, and locations of low intensity in blue, for example. The intensity distribution in the site of interest is expressed by tones of color successively varying from red to blue. For expediency of illustration, FIG. 8 shows a distribution in the form of isobaric lines, locations of high intensity being indicated by solid lines 91, and locations of low intensity by broken lines 92.

In this embodiment, the vector type magnetic sensors have been described. each of which includes three magnetic sensors with the coil planes intersecting at a predetermined angle. This invention is not limited to such construction. For example, the magnetic sensors may be arranged with the coil planes not intersecting one another, or two magnetic sensors may be arranged to have intersecting coil planes.

In equation (6) above, an inverse matrix is calculated after adding a unit matrix I of size $\lambda$ as a predetermined value to $\Gamma$. For example, a symmetric matrix or penalty matrix of size $\lambda$ may be used as the predetermined value.

The present invention may be embodied in other specific forms without departing from the spirit or essential attributes thereof and, accordingly, reference should be made to the appended claims, rather than to the foregoing specification, as indicating the scope of the invention.

What is claimed is:

1. A biomagnetism measuring method for measuring, with a plurality of magnetic sensors arranged adjacent a site of interest of a patient, biomagnetism generated from bioelectric currents flowing in the site of interest, and determining the bioelectric currents based on measured biomagnetism information acquired through the measurement, said method comprising the steps of:

computing transfer constants indicating degrees by which the biomagnetism is transferred from each particular position in said site of interest to each of said magnetic sensors;

regulating a matrix $\Gamma$ of said transfer constants by adding a predetermined value $\lambda I$ to said matrix $\Gamma$;

computing a weight coefficient for each of said magnetic sensors to enhance biomagnetism generated from said particular position, based on virtual biomagnetism information virtually measured by said magnetic sensors and an inverse matrix $(\Gamma+\lambda I)^{-1}$ of said regulated matrix $(\Gamma+\lambda I)$, when a known bioelectric current is set to said particular position;

collecting measured biomagnetism information acquired by measuring the biomagnetism generated from said site of interest with said magnetic sensors;

computing enhanced biomagnetism information having said biomagnetism generated from said particular position enhanced by applying said weight coefficient to said measured biomagnetism information measured by each of said magnetic sensors; and determining a bioelectric current in said particular position based on said enhanced biomagnetism information.

2. A biomagnetism measuring method as defined in claim 1, further comprising the step of outputting an arrow map showing said bioelectric current in each particular position in form of an arrow.

3. A biomagnetism measuring method as defined in claim 1, further comprising the step of outputting an arrow map showing said bioelectric current in each particular position in form of an arrow, as superposed on a tomographic image including said particular position.

4. A biomagnetism measuring method as defined in claim 1, further comprising the step of outputting an intensity distribution chart of the bioelectric currents generated in said site of interest.

5. A biomagnetism measuring method as defined in claim 1, further comprising the step of outputting a waveform chart of biomagnetism measured by each of said magnetic sensors.

6. A biomagnetism measuring method as defined in claim 1, wherein the matrix regulating step is executed to add said predetermined value $\lambda I$ for a solution of said matrix $\Gamma$ of said transfer constants to be remote from zero.

7. A biomagnetism measuring method as defined in claim 6, wherein said predetermined value $\lambda I$ is at least one of a unit matrix or a penalty matrix having a predetermined size.

8. A biomagnetism measuring method as defined in claim 6, wherein said predetermined value $\lambda I$ is at least one of a unit matrix or a penalty matrix having a size corresponding to noise included in said measured biomagnetism information.

9. A biomagnetism measuring apparatus for measuring, with a plurality of magnetic sensors arranged adjacent at site of interest of a patient, biomagnetism generated from bioelecric currents flowing in the site of interest, and determining the bioelectric currents based on measured biomagnetism information acquired through the measurement, said apparatus comprising:

a plurality of magnetic sensors arranged adjacent a site of interest;

transfer constant computing means for computing transfer constants indicating degrees by which the biomagnetism is transferred from each particular position in said site of interest to each of said magnetic sensors;

regulating means for regulating a matrix of said transfer constants by adding a predetermined value $\lambda I$ to said matrix;

weight coefficient computing means for computing a weight coefficient for each of said magnetic sensors to enhance biomagnetism generated from said particular position, based on virtual biomagnetism information virtually measured by said magnetic sensors and an inverse matrix of said regulated matrix, when a known bioelectric current is set to said particular position;

measurement information collecting means for collecting measured biomagnetism information acquired by measuring the biomagnetism generated from said site of interest with said magnetic sensors;

enhanced biomagnetism information computing means for computing enhanced biomagnetism information having said biomagnetism generated from said particular position enhanced by applying said weight coefficient to said measured biomagnetism information measured by each of said magnetic sensors; and bioelectric current computing means for determining a bioelectric current in said particular position based on said enhanced biomagnetism information.

10. A biomagnetism measuring apparatus as defined in claim 9, further comprising output means for outputting an arrow map showing said bioelectric current in each particular position in form of an arrow.

11. A biomagnetism measuring apparatus as defined in claim 9, further comprising output means for outputting an arrow map showing said bioelectric current in said particular position in form of an arrow, as superposed on a tomographic image including said particular position.

12. A biomagnetism measuring apparatus as defined in claim 9, further comprising output means for outputting an intensity distribution chart of the bioelectric currents generated in said site of interest.

13. A biomagnetism measuring apparatus as defined in claim 9, further comprising output means for outputting a waveform chart of biomagnetism measured by each of said magnetic sensors.

14. A biomagnetism measuring apparatus as defined in claim 9, wherein each of said magnetic sensors includes a coil, and a superconducting quantum interference device connected to said coil.

15. A biomagnetism measuring apparatus as defined in claim 9, wherein said regulating means is operable to add said predetermined value for a solution of said matrix of said transfer constants to be remote from zero.

16. A biomagnetism measuring apparatus as defined in claim 15, wherein said predetermined value is at least one of a unit matrix or a penalty matrix having a predetermined size.

17. A biomagnetism measuring apparatus as defined in claim 15, wherein said predetermined value is at least one of a unit matrix or a penalty matrix having a size corresponding to noise included in said measured biomagnetism information.

18. A biomagnetism measuring apparatus as defined in claim 9, further comprising stimulating means for applying at least one of an electric stimulation, an acoustic stimulation and an optical stimulation.

* * * * *